(12) United States Patent
Luo et al.

(10) Patent No.: US 9,163,058 B2
(45) Date of Patent: Oct. 20, 2015

(54) METHOD FOR PREPARING ULIPRISTAL ACETATE AND KEY INTERMEDIATE THEREOF

(75) Inventors: Junzhi Luo, Shanghai (CN); Yongqiang Sun, Jiangsu (CN); Xun Luo, Shanghai (CN); Yimin Yan, Jiangsu (CN); Zhaojun Wang, Shanghai (CN); Mingxia Qian, Jiangsu (CN); Yongrui Tu, Jiangsu (CN)

(73) Assignees: Utopharm (Shanghai) Co., Ltd, Shanghai (CN); Changzhou No. 4 Pharmaceutical Factory Co., Ltd, Changzhou, Jiangsu (CN)

( * ) Notice: Subject to any disclaimer, the term of this patent is extended or adjusted under 35 U.S.C. 154(b) by 0 days.

(21) Appl. No.: 14/233,757

(22) PCT Filed: Jul. 12, 2012

(86) PCT No.: PCT/CN2012/000952
§ 371 (c)(1),
(2), (4) Date: Jan. 19, 2014

(87) PCT Pub. No.: WO2013/063859
PCT Pub. Date: May 10, 2013

(65) Prior Publication Data
US 2014/0296510 A1    Oct. 2, 2014

(30) Foreign Application Priority Data
Jan. 11, 2011   (CN) .......................... 2011 1 0339479

(51) Int. Cl.
*C07J 41/00*   (2006.01)
*C07J 21/00*   (2006.01)
*C07J 7/00*    (2006.01)
*C07J 71/00*   (2006.01)

(52) U.S. Cl.
CPC ............ *C07J 41/0083* (2013.01); *C07J 7/0045* (2013.01); *C07J 21/006* (2013.01); *C07J 41/00* (2013.01); *C07J 41/0094* (2013.01); *C07J 71/001* (2013.01)

(58) Field of Classification Search
CPC ..... C07J 7/0045; C07J 21/006; C07J 41/0083
USPC ..................... 540/36; 552/592, 598
See application file for complete search history.

(56) References Cited

U.S. PATENT DOCUMENTS 4,954,490 A    9/1990   Cook et al.
5,929,262 A    7/1999   Kim et al.

FOREIGN PATENT DOCUMENTS

| CN | 101048394 | 10/2007 |
|---|---|---|
| CN | 101466723 | 6/2009 |
| CN | 101622268 | 1/2010 |
| CN | 102516345 | 6/2012 |
| WO | 2004078709 | 9/2004 |
| WO | 0174840 | 10/2011 |

OTHER PUBLICATIONS

Liu Hongbin et al. Graphical Synthetic Routes of Ulipristal Acetate for Post-coital Antifertility. Chinese Journal of Pharmaceuticals, 201, vol. 42, No. 1, pp. 73-75, 2011.

*Primary Examiner* — Brenda Coleman

(57) ABSTRACT

A method as well as new intermediates for preparing Ulipristal acetate (a compound I) and a method for preparing the new intermediates are provided. The intermediate in a constitutional formula IV is conductive to reacting with methyl lithium or methyl Grignard reagent, a protective group is easy to be removed after a reaction, side reactions are few, a midterm treatment is simple, the reagents used are cheap, costs are low and a yield is high, if a compound in a constitutional formula V is obtained by the reaction of a compound in a constitutional formula III and the intermediate in the constitutional formula IV, the yield of a two-step reaction is 75%, a purity is above 98%.

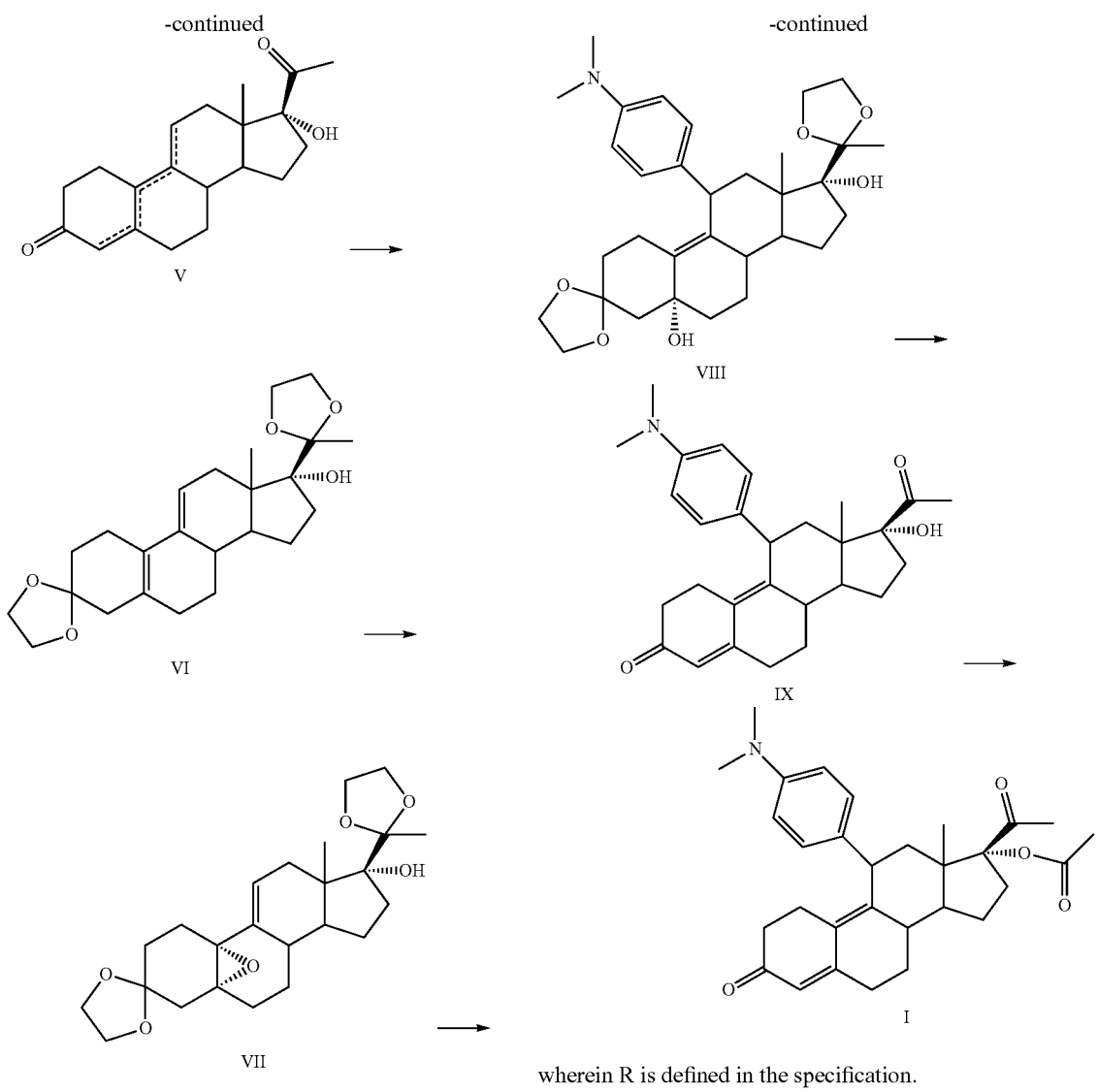
wherein R is defined in the specification.
13 Claims, No Drawings

METHOD FOR PREPARING ULIPRISTAL ACETATE AND KEY INTERMEDIATE THEREOF

CROSS REFERENCE OF RELATED APPLICATION

This is a U.S. National Stage under 35 U.S.C 371 of the International Application PCT/CN2012/000952, filed Jul. 12, 2012, which claims priority under 35 U.S.C. 119(a-d) to CN 201110339479.8, filed Nov. 1, 2011.

BACKGROUND OF THE PRESENT INVENTION

1. Field of Invention

The present invention relates to a medicine, particularly to a method for preparing medicine, and more particularly to a method for preparing ulipristal acetate with an anti-progesterone and anti-glucocorticoid function and to a key intermediate and a preparing method therefor.

2. Description of Related Arts

Ulipristal acetate (a compound I; chemical name: 17α-acetoxyl-11β-(4-N,N-dimethylamino-phenyl)-19-norpregna-4,9-diene-3,20-dione) is a strong anti-progesterone and anti-glucocorticoid medicine. A constitutional formula of the Ulipristal acetate is as follows:

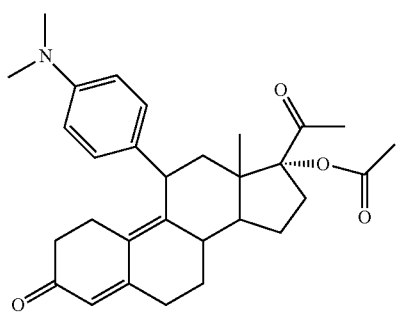

I

The Ulipristal acetate has been approved to be sold in Europe and America for being used within five days after unprotected sex and a known or suspected contraceptive failure, the Ulipristal acetate is an effective and safe emergency contraceptive.

Related reports of methods for preparing the Ulipristal acetate are as follows.

1. A method disclosed in the U.S. Pat. No. 4,954,490, (as illustrated in the equation I)

The method utilizes 3-methoxyl-19-norpregna-1,3,5(10),17(20)-tetraene as a starting material, and after an addition reaction, oxidation, reduction, hydrolysis and an addition-elimination action, 17α-hydroxyl-19-norpregna-4,9-diene-3,20-dione (a compound V2) is obtained by the oxidation, then the Ulipristal acetate (the compound I) is obtained by a total of ten reactions comprising ethylene glycol condensation, m-chloroperoxy benzoic acid epoxidation, Grignard addition, acid hydrolysis and acetylation, and a product with a melting point of 118~121° C. is obtained by water/methanol recrystallization. The method is not adaptable to an industrialized production because the steps of the method are too many, the starting material is not easy to be obtained, reaction conditions are complex, intermediates need to be chromatography purified, a its total yield is only 0.62%, costs are very high and the product is not stable enough to be utilized in the medicine;

the equation I:

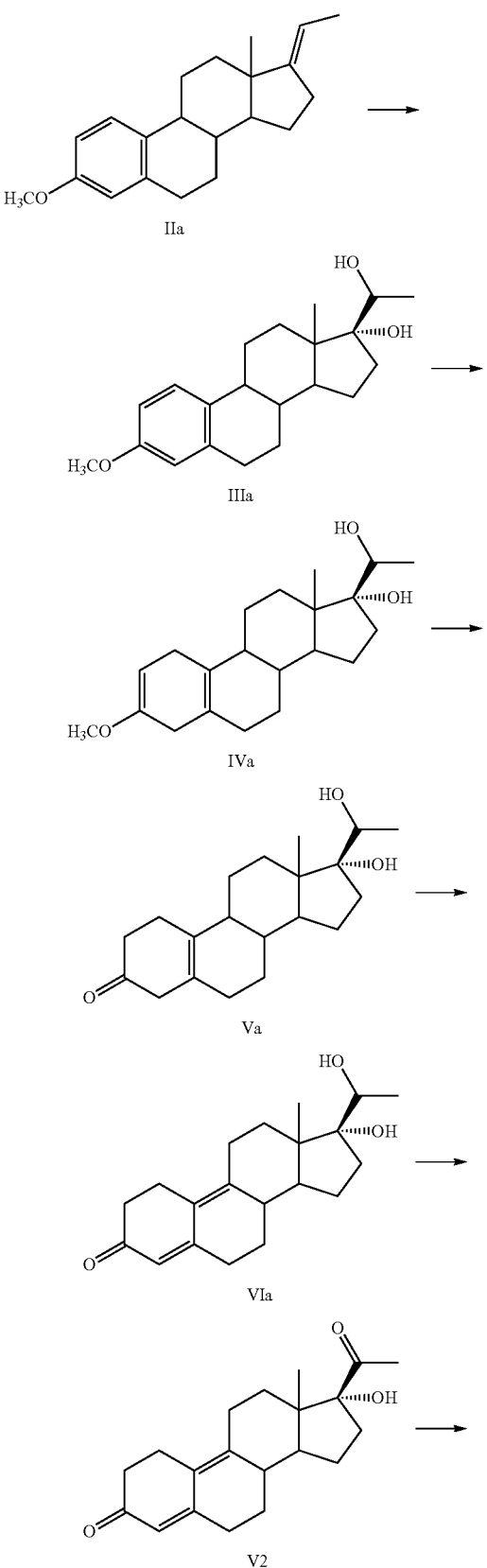

-continued
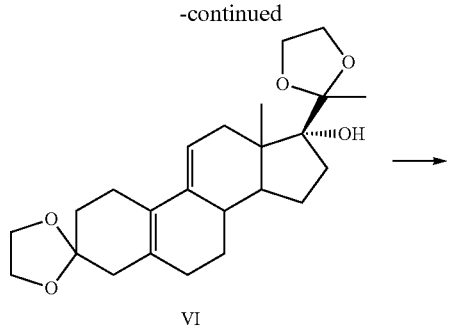
VI
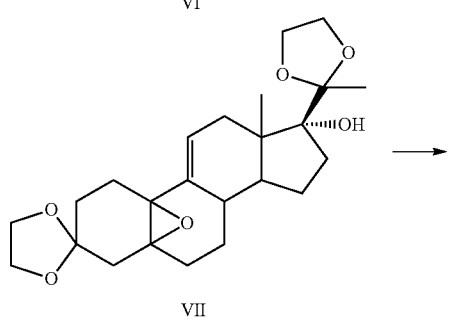
VII
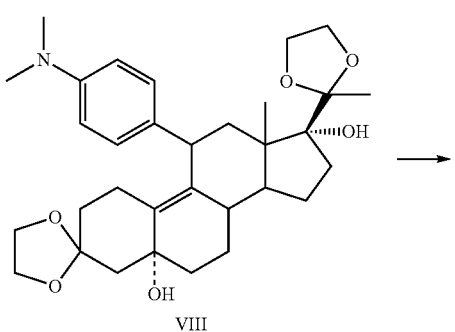
VIII
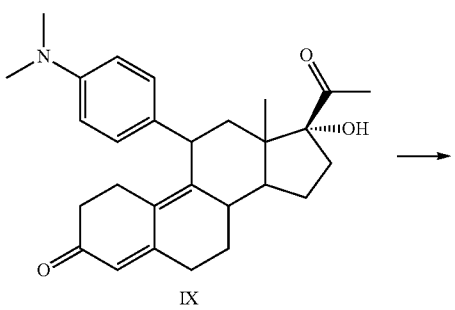
IX
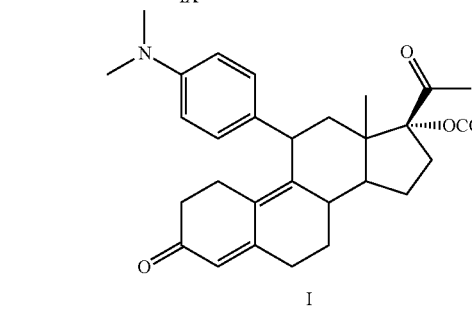
I
2. Another method disclosed in the U.S. Pat. No. 5,929,262 (as illustrated in the equation II)
the equation II:
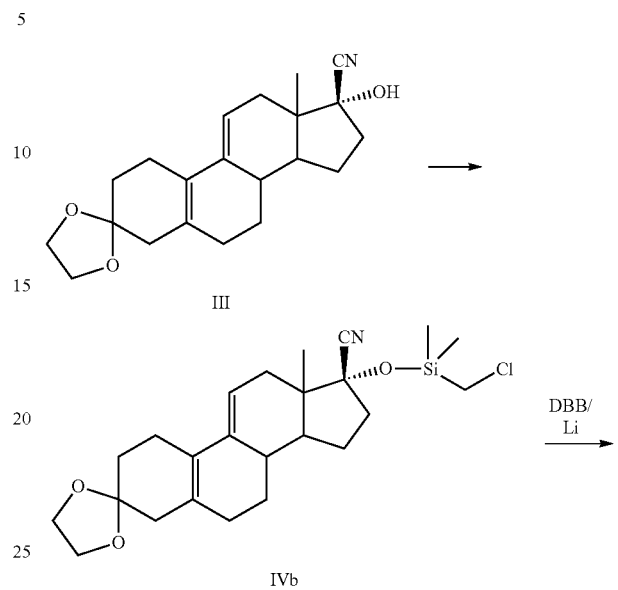
III
IVb
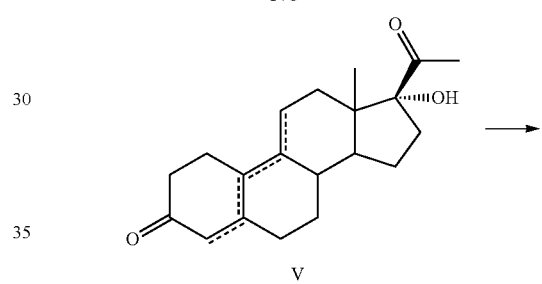
V
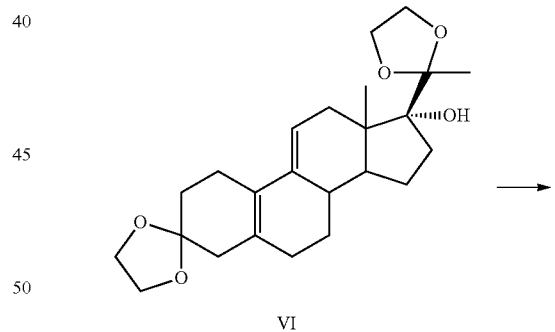
VI
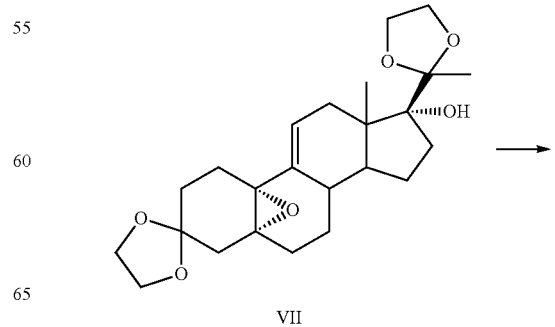
VII -continued

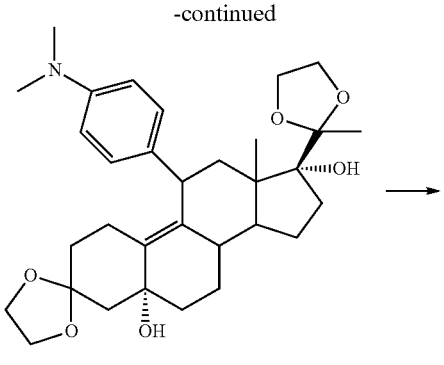
VIII

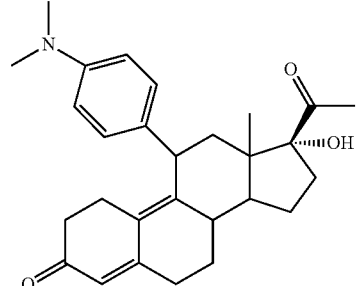
IX

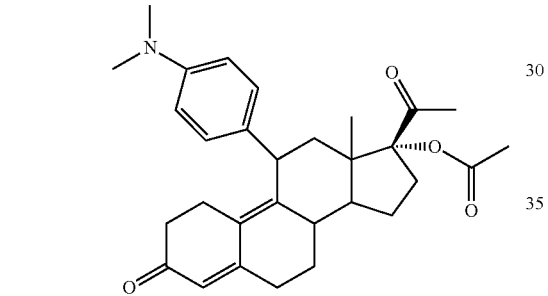
I the method utilizes 3,3-ethylendioxyl-17β-cyano-19-norpregna-5(10),9(11)-diene-17α-alcohol (a compound III) as the starting material, and 17α-hydroxy is protected by dimethyl chloromethyl silicane, the starting material is acid hydrolyzed after a reaction with a DBB/Li reagent at a low temperature of −70° C., then diketal is obtained by the ethylene glycol condensation reaction, a desired product is obtained by the epoxidation reaction, the Grignard reaction, the acid hydrolysis reaction and the acetylation reaction, and a yellow product with a melting point of 183~185° C. is obtained by isopropanol, ethyl acetate and ethyl ether crystallization treatments. The method also does not adapt to the industrialized production because a cost of the starting material and DBB are very high, the reaction conditions are strict, an ultra low temperature and anhydrous anaerobic reaction are needed, the yield is low (wherein the total yield is only 14%) and the costs are also very high.

3. A third method was disclosed in the PCT application WO2004078709, (as illustrated in the equation III), a desired product is obtained by utilizing 17α-hydroxyl-19-norpregna-4,9(10)-diene-3,17-dione (a compound V2) with the acetylization, 3-carbonyl condensation, the epoxidation and the hydrolysis. A route of synthesis is simple, but the starting material is prepared from a compound VI by hydrolysis under an acidic condition, the total yield is only 11.8% (calculated from the compound VI), and in fact, the steps are much more, the yield is lower and the costs are higher, therefore, the method is not adaptable to the industrialized production;

the equation III:

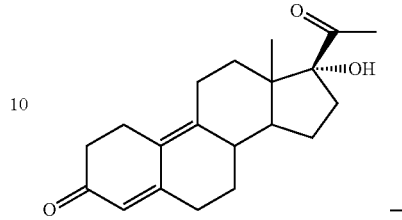
V2

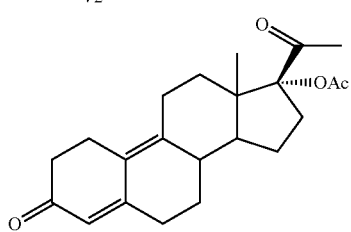
IIIc

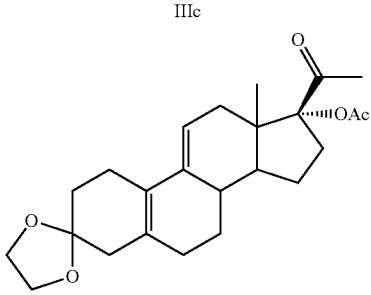
IVc

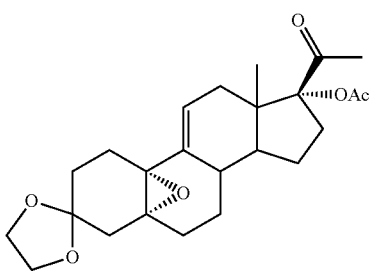
Vc

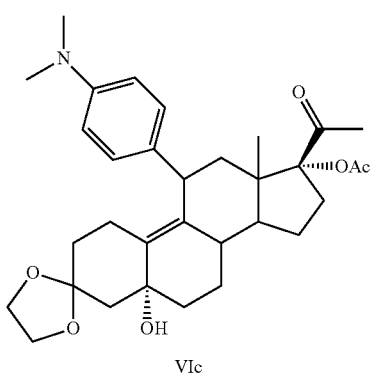
VIc

-continued
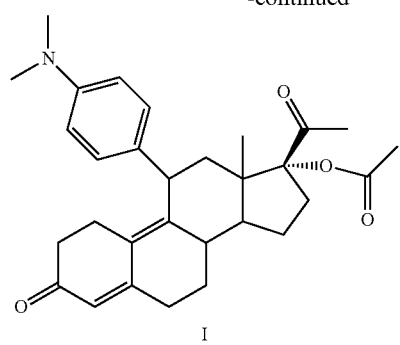
I
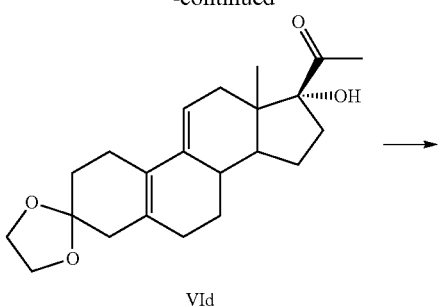
VId
4. A method was disclosed in the Chinese patent application CN200780021915.9 (as illustrated in the equation IV);
the equation IV:
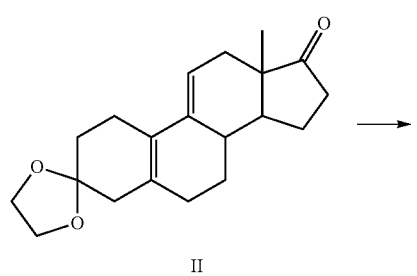
II
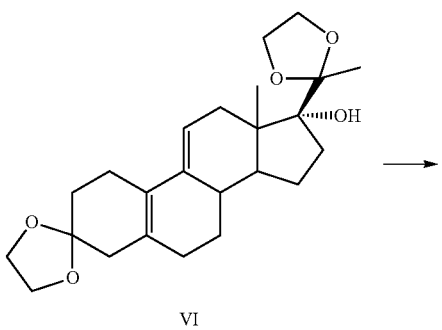
VI
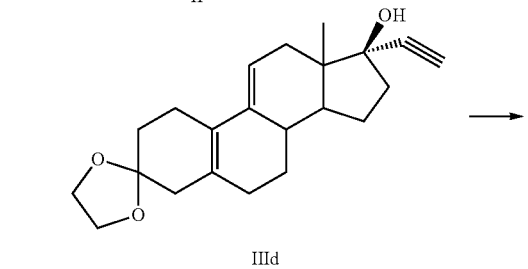
IIId
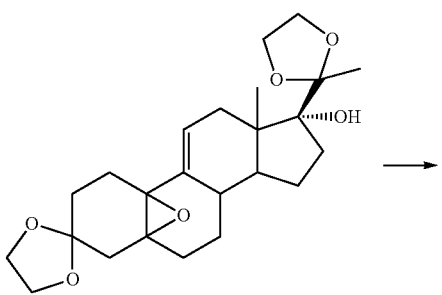
VII
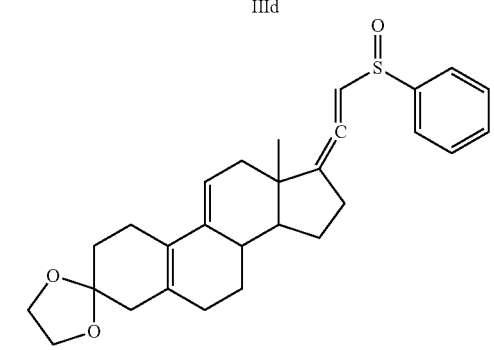
IVd
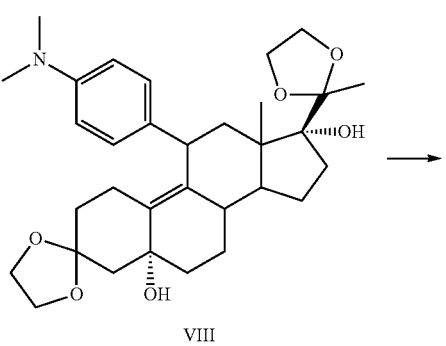
VIII
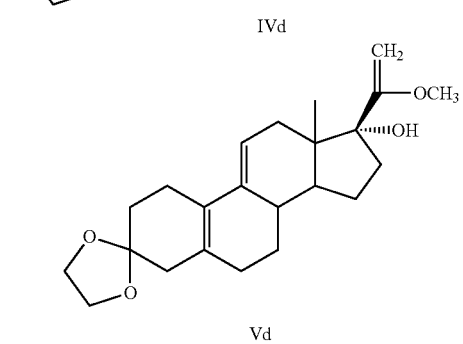
Vd
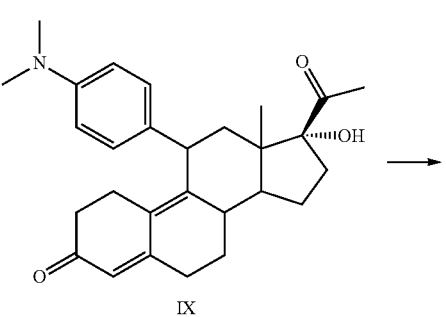
IX

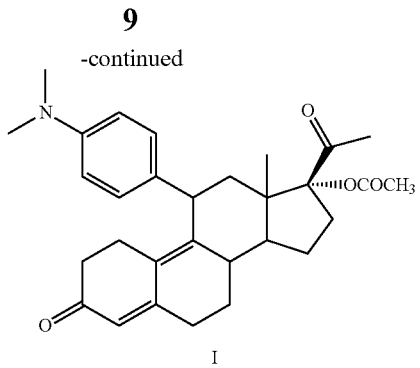

I the method utilizes 3,3-ethylendioxyl-19-norpregna-5 (10),9(11)-diene-17-one (3-Ethylene Ketal for short, a compound II) as the starting material, the desired product is obtained by a total of nine reactions comprising the acetylene addition reaction, reaction with phenylsulfenyl chloride, the sodium methoxide hydrolysis, the acid hydrolysis, the ethylene glycol condensation, the epoxidation, the Grignard reaction, the acid hydrolysis and the acetylation reaction, solvate-free crystals are obtained after the isopropanol crystallization and being heated by ethanol and water for 14 h at 70° C. The method utilizes acetylene with great danger and the phenylsulfenyl chloride with a stink, wherein the phenylsulfenyl chloride is not stable and not easy to be stored, and impurities produced by decomposition involved in the reactions will lead to the low yield, additionally, the phenylsulfenyl chloride can deeply pollute environments, and new impurities is produced by being heated for a long time at the high temperature in the crystallization reaction, the total yield of the method is 13.8%~15.8%, the costs are high, therefore, the method is not adaptable to the industrialized production.

In the conventional methods as above, the method 1, 2 and 4 are related to preparation of the compound VI, and the starting material of the method 3 is hydrolyzed from the compound VI.

SUMMARY OF THE PRESENT INVENTION

An object of the present invention is to provide an industrialized method without above shortcomings for preparing Ulipristal acetate.

Accordingly, in order to accomplish the above object, the present invention provides a method for preparing the Ulipristal acetate, and new key intermediates for preparing the Ulipristal acetate.

The method of the present invention utilizes 3-Ethylene Ketal (a compound II) capable of being easily obtained in China as a starting material, 17β-cyano group (a compound III) is obtained by an addition reaction in an solvent of the 3-Ethylene ketal with a cyanation reagent, 17α-hydroxy of the compound III is protected and a compound IV is obtained, a compound V is obtained by acid hydrolyzing the compound IV after the compound IV reacts with methyl lithium or a methyl Grignard reagent, 3,3,20,20-bis(ethylendioxyl)-17α-hydroxyl-19-norpregna-5(10),9(11)-diene (a compound VI) is obtained after the compound V reacting with ethylene glycol in a presence of a p-toluenesulfonic acid and trimethyl orthoformate or triethyl orthoformate, then 3,3,20,20-bis (ethylendioxyl)-17α-hydroxyl-5α,10α-epoxy-19-norpregna-9(11)-ene (a compound VII) is obtained by oxidizing the compound VI with hydrogen peroxide, 3,3,20,20-bis(ethylendioxyl)-5α-17α-dihydroxyl-11β-[4-(N,N-dimethylamino)-phenyl-]-19-norpregna-9(11)-ene (a compound VIII) is obtained by Grignard reaction of the compound VII and 4-(N,N-dimethylamino)phenylmagnesium bromide Grignard reagent, 17α-hydroxy-11β-[4-(N,N-dimethylamino)-phenyl-]-19-norpregna-9(11)-diene-3,20-dione (compound IX) is obtained by hydrolyzing the compound VII under an acid condition, the Ulipristal acetate (a compound I) is obtained after the compound IX reacts with an acetylation reagent comprising anhydrous acetic acid, perchloric acid and acetic anhydride, reaction step of the method for preparing the Ulipristal acetate (a compound I) is recrystallized with an ethanol:isopropanol (0.5~1:9), the route of synthesis is as follows:

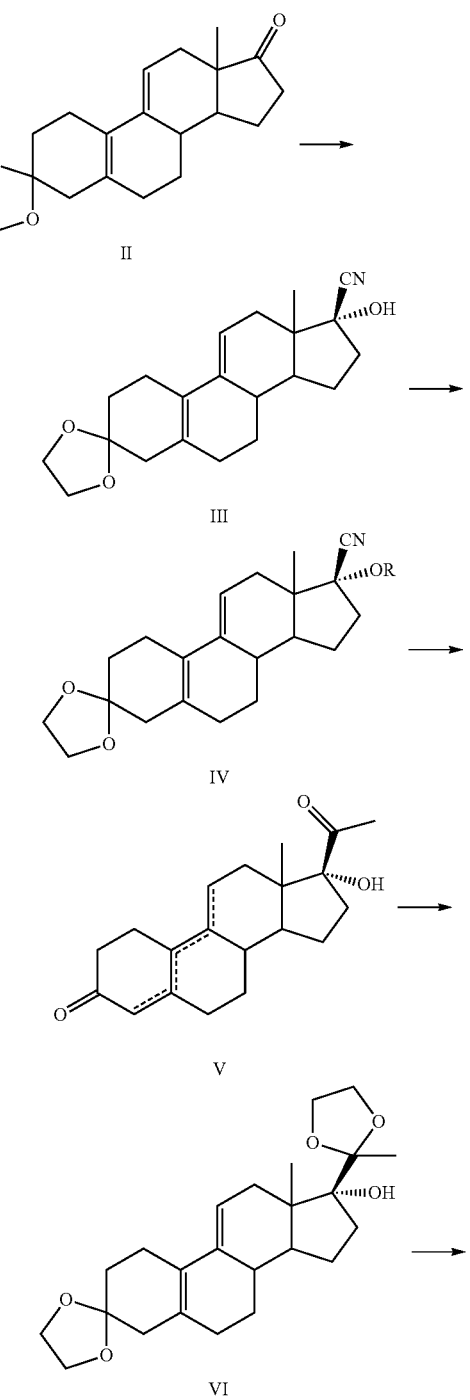

-continued

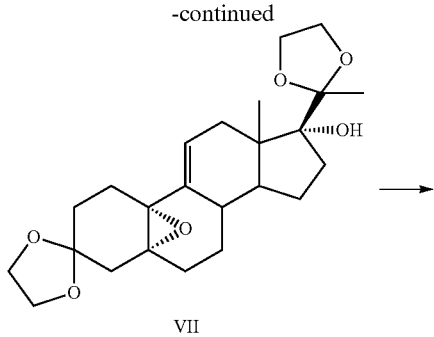

VII

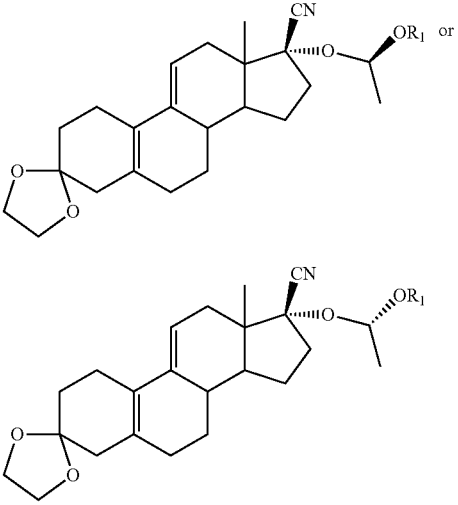

VIII

IX

I wherein R is a hydroxy protective group, and is selected from —CR$_3$(R$_4$)R$_5$, —COR$_2$ or 2-tetrahydropyran; wherein the R$_3$, R$_4$ and R$_5$ are selected respectively from hydrogen, hydroxyl, halogen, OR$_1$, substituted or unsubstituted C1-C10 alkyl; the R$_1$ and R$_2$ are selected respectively from substituted or unsubstituted C1-C10 alkyl; substituent is selected from hydroxyl, halogen, nitro group or amidogen;

dotted lines in a constitutional formula V represents that locations of double bonds are at 5(10), 9(11) or 4(5), 9(10);

preferably, wherein the R is the hydroxy protective group, and is selected from —CH(CH$_3$)OR$_1$, —COR$_2$ or 2-tetrahydropyran, the R$_1$ and R$_2$ are selected respectively from C1-C10 alkyl or aryl radical;

wherein when the R is —CH(CH$_3$)OR$_1$, —COR$_2$ or 2-tetrahydropyran, compounds in the constitutional formula IV comprises an isomer compound IV1, IV2, IV3 or IV4 or racemic modifications thereof, the detailed constitutional formula is as follows:

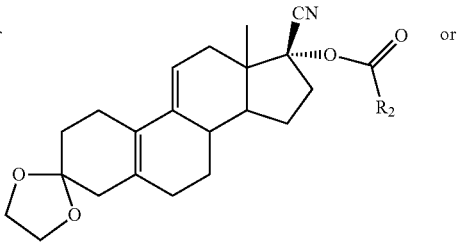

or racemic modifications;

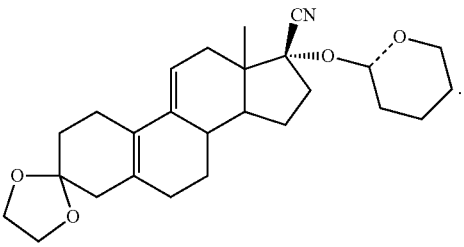

The R$_1$ and R$_2$ are defined as above. Dot and line keys are respectively a R or S configuration or the racemic modifications.

Preferably, the $R_1$ and $R_2$ are selected from compounds as follows:

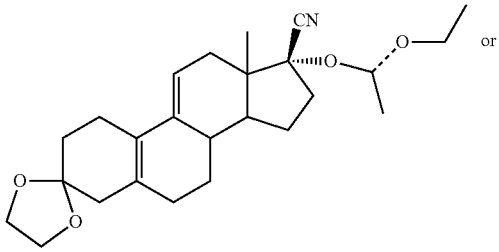

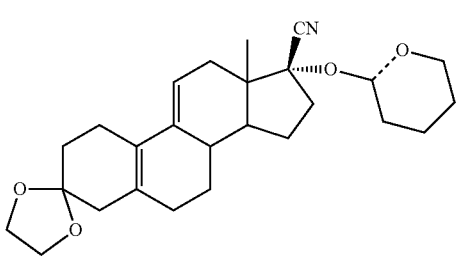

IV4 the dot and line keys are respectively the R or S configuration or the racemic modifications.

Specifically, the method of the present invention comprises steps of:

a) utilizing 3,3-ethylendioxyl-19-norpregna-5 (10),9 (11)-diene-17-dione (3-Ethylene Ketal for short) as a raw material and utilizing alcohols as a reacting solvent, wherein a 17β-cyano group compound III is selectively obtained by a reaction of the starting material and a cyanation reagent under a acid condition at a temperature between −10° C. to room temperature; wherein the alcohols reaction solvent is selected from methanol, ethanol and isopropanol, and the methanol is preferred; the cyanation reagents are selected from sodium cyanide, potassium cyanide, acetone cyanohydrin and hydrogen cyanide, etc, and the sodium cyanide and the potassium cyanide are preferable choices; the acid is preferably selected from formic acid or anhydrous acetic acid; the reacting temperature is preferably selected from −10~25° C., a mole ratio of the starting material and the cyanation reagents is 1:1.1~1.5, a reacting time is 2~24 h;

b) obtaining the compound IV by the reaction of the compound III and a hydroxy protective group reagent under the acid condition in a solvent; wherein the solvent is selected from halogenated hydrocarbon such as dichloromethane and chloroform, or ether such as THF (tetrahydrofuran), ethyl ether or isopropyl ether, the solvent is preferably selected from the dichloromethane, the THF or the ethyl ether; the hydroxy protective group reagents are selected from organosilyl matter such as trimethylsilyl lithium, trimethyl chlorosilane and chlorochloromethyl dimethylsilane, or vinyl ether $CH_2=CHOR_1$ such as ethyl vinyl ether, n-propyl vinyl ether, n-butyl vinyl ether and methyl vinyl ether, or carboxylic acid anhydride such as acetic anhydride and propanoic anhydride, or carboxylic acid, acyl chloride, etc., or 2,3-dihydropyran, etc., the hydroxy protective group reagents are preferably selected from the ethyl vinyl ether or the 2,3-dihydropyran; the acid is selected from p-toluenesulfonic acid, an amount of the acid is 0.1%~5% W/W of an amount of the compound III; the reacting temperature is between −20 and 50° C., the mole ratio of the starting material and the hydroxy protective group reagent is 1:1.1~2, the reacting time is 0.5~24 h;

c) hydrolyzing the compound IV under the acid condition after the reaction of the compound IV with a methylation reagent for obtaining the 5(10),9(11)-diene-3,20-dione compound V1 or 4,9(10)-dienen-3,20-dione compound V2 or a mixed compound V comprising the compound V1 and compound V2, wherein the reacting solvent is selected from ether such as diethyl ether, isopropyl ether or THF; or halogenerated hydrocarbon of dichloromethane or chloroform, the reacting solvent is preferably selected from diethyl ether, THF or dichloromethane; the methylation reagent is selected from methyl lithium or methyl Grignard reagent, and is preferably selected from methyl lithium; the reacting temperature is −30° C. to a reflux temperature and preferably the room temperature; the mole ratio of the starting material and the methylation reagent is 1:1.1~5, and preferably 2~3 equivalents; the reacting time is 0.5~24 h; the solvent for hydrolyzing under the acid condition is selected from acetone or butanone; methanol or ethanol; diethyl ether, THF, ethylene glycol or dimethyl ether; acetic ether or menthyl acetate; or dichloromethane or chloroform; the reagent is preferably selected from butanone, methanol, THF or diethyl ether, wherein icy water is added for quenching after the reaction, then the acid is directly added for hydrolyzing, or an extracting reagent insoluble in water is added for extracting, wherein the extracting reagent is selected from the halogenerated hydrocarbon such as the dichloromethane or the chloroform, or an esters solvent such as the acetic ether or the menthyl acetate, or the ether such as the diethyl ether or the isopropyl ether, or an arene reagent such as benzene or methylbenzene; the acid is directly added for hydrolyzing after extraction, or a reagent soluble in water and the acid are added for hydrolyzing after concentrating, wherein the acid utilized in hydrolyzing is selected from mineral acids such as sulphuric acid, hydrochloric acid, potassium bisulfate or sodium bisulfate, or organic acids such as formic acid or acetic acid, 1~6N hydrochloric acid is a preferable choice; a hydrolyzing temperature is −40~100° C., preferably 25~50° C., the invention further discloses that by controlling the hydrolyzing temperature, a main product of the hydrolysis is the compound V1, and then the compound V1 is slowly transformed to the more stable compound V2, or the pure compound V2 can be obtained by crystallizing with the solvent such as methanol, etc; in fact, a ratio of the compound V1 and V2 can be modified freely by controlling the hydrolysis conditions such as acidity, the temperature and the reacting time, but the ratio has no effect on the next step; taking the ethyl vinyl ether as the protective group is an example, the compound in the constitutional formula IV is hydrolyzed and transformed into imine after the addition reaction with the methyl lithium or methyl Grignard reagent, the compound V (the compound V is the compound V1, the compound V2 or a mixture of the compound V1 and V2) is obtained after the imine is further hydrolyzed,

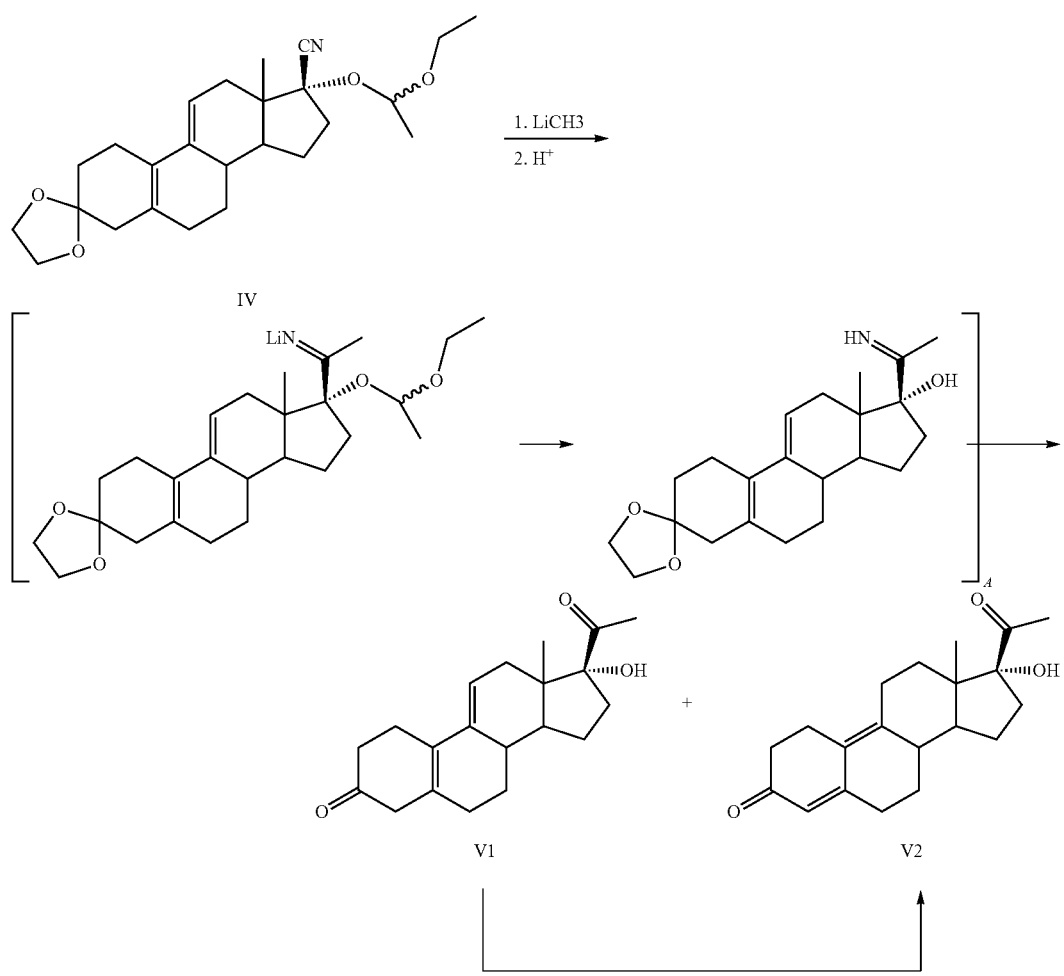

additionally, in the procedure of the step c), the compound IV can be involved in a next step reaction as a single isomer or a mixture of isomers, preferably the mixture of isomers;

d) catalyzing the reaction of the compound V and the ethylene glycol on the presence of the p-toluenesulfonic acid and the trimethyl orthoformate or the triethyl orthoformate at the room temperature for obtaining the 3,20-diketal compound VI, wherein the solvent is preferably selected from dichloromethane, the reacting temperature is 0° C. to the room temperature, the reacting time is 1~8 h;

e) dissolving the compound VI in the dichloromethane and then adding an oxidant and perhalogeno-acetone under an alkaline condition at the room temperature for reacting in such a manner that the compound VII is obtained, wherein an alkali is selected from pyridine, dipotassium phosphate, monopotassium phosphate, diposodium phosphate, monosodium phosphate, etc.; the oxidant is selected from hydrogen peroxide, m-chloroperoxybenzoic acid, etc., preferably hydrogen peroxide; the reacting temperature is −10~10° C.;

f) catalyzing the addition reaction of the compound VII and a 4-(N,N-dimethyl amidogen)phenylmagnesium bromide Grignard reagent in the presence of cuprous chloride catalyst for obtaining the compound VIII, wherein the mole ratio of the starting material and the Grignard reagent is 1:1.5~5, the reacting temperature is −10~40° C., the reacting time is 2~8 h;

g) hydrolyzing the compound VIII in the dichloromethane and dilute acid at 0~25° C. with stirring for obtaining the compound IX, wherein the acid is selected from the mineral acids such as hydrochloric acid, sulphuric acid or sodium bisulfate, preferably 0.2~4N HCl solvent, the reacting temperature is −10~50° C., the reacting time is 1~5 h;

h) acetylating the compound IX with the anhydrous acetic acid, perchloric acid or acetic anhydride, preferably the perchloric acid and the acetic anhydride mixed with the acetic acid for obtaining the Ulipristal acetate (compound I); wherein the reacting temperature is −40~25° C., preferably −10~25° C.; the ratio of the acetic acid is 1~50% V/V, preferably 10-15% V/V, of the acetylation reagent comprising the acetic acid, the perchloric acid and the acetic anhydride, the reaction can be presented at 0~25° C. without side reactions once the acetic acid is added, however, the similar reaction in the reference CN200780021915.9 need to be presented at −30~−20° C.; and i) crystallizing the crude Ulipristal acetate with the ethanol and the isopropanol for obtaining the Ulipristal acetate with a purity of over 99%;

wherein in the step b), a method for preparing a key intermediate of the Ulipristal acetate in the constitutional formula IV is provided;

wherein in the step c), a method for preparing another key intermediate compound of the Ulipristal acetate in the constitutional formula V is provided.

A preferred embodiment of the present invention for preparing the key intermediate compound in the constitutional formula V is provided, wherein the compound III reacts with the hydroxy protective group reagent for obtaining the compound in the constitutional formula IV, the alkali is directly added for modifying a pH value to 7~8 without separation, then the compound IV reacts with the methyl lithium or the methyl Grignard reagent, the product is hydrolyzed in the solvent under the acid condition right after the reaction or after being processed for obtaining the compound V; wherein the hydroxy protective group reagent is selected from the acid anhydride, the acid or the acyl chloride, vinyl ether such as ethyl vinyl ether, n-propyl vinyl ether, n-butyl vinyl ether, isobutyl vinyl ether and methyl vinyl ether, or 2,3-dihydropyran, etc.

Another preferred embodiment of the present invention for preparing the Ulipristal acetate is provided, wherein the compound VI continuously reacts without separating the various intermediates for obtaining the Ulipristal acetate, the target product is obtained by an one-pot reaction from the step f) to the step i) with a high yield. Detailed steps are concentrating epoxide to a proper volume after the epoxidation reaction, modifying the pH value to 1~2 after reacting with the Grignard reagent and being quenched by an aqueous solution of ammonium chloride, stirring for 1~2 h for hydrolyzing, then extracting by the dichloromethane, washing, being dried by anhydrous magnesium sulfate, being acetylated by the acetylation reagent right after filtering for obtaining the target product, the Ulipristal acetate compound I.

The invention further discloses that the intermediate in the constitutional formula IV is conductive to reacting with the methyl lithium or the methyl Grignard reagent, the reaction condition is mild, the protective group is easy to be removed after the reaction, the side reactions are few, a post treatment is simple, the yield is high, the reagents are cheap and costs are low. For example, when the hydroxyl protective group reagent of the 17α-hydroxy is selected from ethyl vinyl ether or 2,3-dihydropyran, the compound V is obtained by the reaction of the compound III and the intermediate in the constitutional formula IV, the yield of a two-step reaction is 70~75%, the purity is above 98%. Obviously, the intermediate in the constitutional formula IV is the key intermediate for preparing the Ulipristal acetate, and is an important part of the present invention.

The yield of the 3,20-dione (the compound VI) increases by utilizing the key intermediate compound in the constitutional formula IV for preparing the Ulipristal acetate of the present invention, the yield of the compound II to the compound VI is 68%, the costs are low.

Obviously, the procedure of the present invention is simple, there are totally eight steps, the reaction condition is mild and is conductive to reacting, the total yield is about 25~27%. In fact, the compound IV doesn't need to be separated and the Ulipristal acetate could be prepared with the high yield by the one-pot reaction from the step f) to the step i). As a result, only the isolation of three intermediates of the compound III, V and VI are necessary. The operation is simple and is adaptable to the industrialized production.

The present invention also provided a method for purifying the Ulipristal acetate, wherein the method comprises steps of: adding a hot solvent of ethanol:isopropanol (0.5~1:9) into the crude ulipristal acetate, wherein the solvent is 5~20 times of the crude Ulipristal acetate; cooling the hot solvent to 0~25° C. for crystallizing, wherein the product has the purity of 99%.

Therefore, the processing of the present invention is simple, and the reaction condition is mild with high yield. The purity of obtained product is high. Moreover, the reagents are cheap and easy to be obtained. As a result, our costs are low.

The present invention is adaptable to the industrialized production and has a high value in an industrial application.

These and other objectives, features, and advantages of the present invention will become apparent from the following detailed description, the accompanying drawings, and the appended claims.

DETAILED DESCRIPTION OF THE PREFERRED EMBODIMENT

The present invention is further illustrated, but not limited, by following preferred embodiments, wherein:

HNMR is Varian INOVA-400 nuclear magnetic resonance spectrometer testing.

Monocrystal testing utilizes a Bruker SMART APEX-II monocrystal X ray diffractometer; testing requirements is: a CuKa radiation, a graphite monochromator, a diameter of a single vessel φ=0.50 mm, a detector distance between a crystal and a CCD detector d=60.3 mm, a 40 kV tube voltage, a 30 mA tube current; a scan mode is: Φ/w scanning.

A preferred embodiment 1, preparing 3,3-(ethylene-dioxy)-17β-cyano-17α-hydroxy-19-norpregna-5(10),9(11)-diene (a compound III):

adding 3-Ethylene ketal (2.0 kg, 6.37 mol), methanol (12 L), sodium cyanide (343 g, 7.0 mol) and anhydrous acetic acid (440 ml) in a reaction bulb at a room temperature, adding icy water and filtering the reaction mixture by stirring for 30 min, wherein the precipitated crystalline product is filtered off, washing a filter cake three times with water, then drying the filter cake for obtaining 2.06 kg white powder, wherein a mp: 176~178° C. (decomposed), a yield is 95%, HPLC purity is above 98%;

MS: 342(M+1);

an absolute configuration of the compound III is illustrated according to the monocrystal testing:

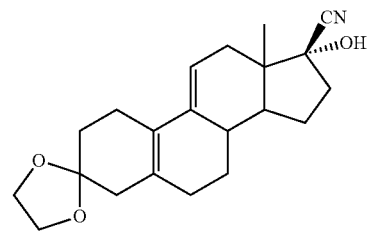 [SMILES: CC12CC=C3C4=C(CCC3C1CC[C@]2(O)C#N)CC1(CC4)OCCO1]

III

A preferred embodiment 2, preparing 17α-[(±)1-(1-ethoxyl)ethyl]oxyl-17β-cyano-3,3-(ethylene-dioxy)-19-norpregna-5(10),9(11)-diene:

adding the compound III (2.0 kg, 5.87 mol) obtained from the preferred embodiment 1 into THF (14 L) and p-toluenesulfonic acid (12.0 g, 70 mmol), adding methyl vinyl ether (668 ml, 7.04 mol) at the room temperature and cooling in the icy water. then stirring with a temperature kept for 4 h, adding triethylamine (15 ml) and the water and stirring for 10 min, extracting an aqueous phase by dichloromethane, combining an organic phase and washing with water, drying by anhydrous magnesium sulfate, decompressing and concentrating in vacuo for obtaining 2.43 kg off-yellow or colourless oil, wherein the yield is quantified (the yield is 100%);

wherein the oil is displayed as two compounds by a TLC (ethyl acetate:petroleum ether=1:5), a solid is precipitated by freezing the oil, products crystallized from ethyl acetate:Petroleum ether (1:2) is mainly high polarity products, HPLC>90%; separating a small amount of the products by a chromatography (with 300~400 mesh numbers) for obtaining a compound IV1 (with a low polarity) and a compound IV2 (with a high polarity);

wherein the compound IV1 is the off-yellow oil: MS: 315 (M+1), 651 (2M+Na); ¹HNMR (CDCl₃): 0.96 (d, 3H)), 1.20 (t, 3H), 1.24-1.34 (m), 1.37 (d, 3H) 1.44-1.50 (m, 1H), 1.52 (s, 1H), 1.75-1.97 (m, 8H), 2.14-2.22 (m), 2.28 (s, 2H), 2.50-2.70 (m), 3.46-3.60 (m), 4.0 (s, 4H), 5.10 (q, 1H), 5.60 (d, 1H);

wherein the compound IV2 is a white crystal: the melting point: 131~134° C.; MS: 315 (M+1), 651 (2M+Na); ¹HNMR (CDCl₃): 0.97 (d, 3H)), 1.26 (t, 3H), 1.33 (d, 3H), 1.45-1.49 (m), 1.52 (s, 1H), 1.77-1.97 (m, 8H), 2.13-2.28 (m, 6H), 2.52 (d, 1H), 2.77 (d, 1H), 3.55-3.74 (m, 2H), 3.98 (s, 4H), 5.02 (q, 1H), 5.59 (d, 1H).

A preferred embodiment 3, preparing the 17α-[(±)1-(1-ethoxyl)ethyl]oxyl-17β-cyano-3,3-(ethylene-dioxy)-19-norpregna-5(10),9(11)-diene:

adding the compound III (50.0 g, 0.147 mol) obtained from the preferred embodiment 1, the dichloromethane (500 ml) and the p-toluenesulfonic acid (0.3 g, 1.74 mmol) and cooling in the icy water, then stirring with the temperature kept for 4 h after methyl vinyl ether (17 ml, 0.18 mol) is added at the room temperature, wherein 60.7 g the off-yellow oil, the 17α-[(±)1-(1-ethoxyl)ethyl]-17β-cyano-3,3-ethylendioxyl-19-norpregna-5(10),9(11)-diene, is obtained by the same operations in the preferred embodiment 2, the yield is quantified, the oil is displayed as the two compounds by the TLC, a result of constitution identifying is the same as the result in the preferred embodiment 2.

A preferred embodiment 4, preparing 17α-[(±)1-(1-n-propyl oxyl)ethyl]oxyl-17β-cyano-3,3-(ethylene-dioxy)-19-norpregna-5(10),9(11)-diene:

utilizing n-propyl vinyl ether as a raw material, wherein the off-yellow oil is obtained by treatments the same as in the preferred embodiment 3, the yield is quantified; the oil is displayed as two compounds by the TLC;

MS: 324 (M-OCH (OC₃H₇) CH₃), 368 (M-OC₃H₇), 450 (M+Na), 877 (2M+Na).

A preferred embodiment 5, preparing 17α-[(±)1-(1-n-butyl oxyl)ethyl]oxyl-17β-cyano-3,3-(ethylene-dioxy)-19-norpregna-5(10),9(11)-diene:

utilizing n-butyl vinyl ether as the starting material, wherein the off-yellow oil is obtained by the treatments the same as in the preferred embodiment 3, the yield is quantified; the oil is displayed as two compounds by the TLC;

MS: 324 (M-OCH (OC₄H₉) CH₃), 368 (M-OC₄H₉), 464 (M+Na), 905 (2M+Na).

A preferred embodiment 6, preparing 17α-[(±)1-(1-isobutyloxyl)ethyl]oxyl-17β-cyano-3,3-(ethylene-dioxy)-19-norpregna-5(10),9(11)-diene:

utilizing isobutyl vinyl ether as the starting material, wherein the off-yellow oil is obtained by the treatments the same as in the preferred embodiment 3, the yield is quantified; the oil is displayed as two compounds by the TLC;

MS: 324 (M-OCH (OC₄H₉) CH₃), 368 (M-OC₄H₉), 464 (M+Na), 905 (2M+Na).

A preferred embodiment 7, preparing 17α-[(±)1-(1-tetrahydropyran)ethyl]oxyl-17β-cyano-3,3-(ethylene-dioxy)-19-norpregna-5(10),9(11)-diene:

utilizing dihydropyran as the starting material, wherein the off-yellow oil is obtained by the treatments the same as in the preferred embodiment 3, the yield is quantified; the oil is displayed as two compounds by the TLC;

MS: 426 (M+1), 873 (2M+Na).

A preferred embodiment 8, preparing a compound V:

adding 17α-[(±)1-(1-ethoxyl)ethyl]oxyl-17β-cyano-3,3-(ethylene-dioxy)-5 (10), 9(11)-dien (12.0 g, 29 mmol), anhydrous THF (120 ml) in the reaction bulb and cooling in the icy water, then stirring at 0~10° C. for 4 h after 1.0M methyl lithium 2-methyl tetrahydrofuran (58 ml, 58 mmol) is added at 0~10° C., adding 50 ml water and stirring for 10 min, separating out an organic phase and extracting the aqueous phase by the ethyl acetate, combining the organic phase with the aqueous phase, decompressing and concentrating in the vacuo, then adding 50 ml methanol and 2N HCl and stirring for 2 h at 25° C., and pouring the reaction mixture into the icy water and separating out the organic, extracting the aqueous phase by the ethyl acetate, combining the organic phase, drying, filtering, and concentrating in the vacuo for obtaining 6.6 g off-yellow powder, wherein the mp: 184~188° C., the yield is 73%, the powder is displayed as two compounds by the TLC (ethyl acetate:petroleum ether=1:2);

wherein ethyl acetate:petroleum ether=1:5 is utilized as an eluant, products are separated by the chromatography for obtaining a compound V1 (with a low polarity) and a compound V2 (with a high polarity), a sample for analyzing is crystallized by the ethyl acetate, wherein the ethyl acetate is 5 times of the products;

wherein the compound V1 is the off-yellow powder, the MP: 196~200° C.;

MS: 15(M+1); ¹HNMR (CDCl₃): 0.71 (s, 3H), 1.28-1.48 (m, 2H), 1.64 (m, 1H), 1.75-1.81 (dd, 1H), 1.89-2.02 (m, 5H), 2.22-2.24 (br, 1H), 2.27 (s, 3H), 2.45-2.53 (m, 3H), 2.67-2.80 (m, 3H), 2.80 (s, 1H), 2.86 (brs, 2H), 5.62 (d, 1H);

the absolute configuration of the compound V1 is illustrated according to the monocrystal testing:

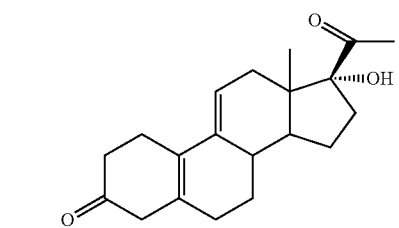 [SMILES: CC(=O)[C@@]1(O)CCC2C3CCC4=C(CCC(=O)C4)C3=CCC21C]

wherein the compound V2 is the off-yellow powder, the MP: 197~202° C.;

MS: 315(M+1); ¹HNMR (CDCl₃): 0.87 (s, 3H), 1.34-1.46 (m, 2H), 1.48-1.53 (m, 1H), 1.59-1.66 (m, 1H), 1.83-1.96 (m, 4H), 2.10 (dt, 1H), 2.26-2.30 (s, 3H, m, 1H), 2.2-2.56 (m, 5H), 2.73 (dt, 1H), 2.81-2.91 (m, 3H), 5.67 (s, 1H);

the absolute configuration of the compound V2 is illustrated according to the monocrystal testing:

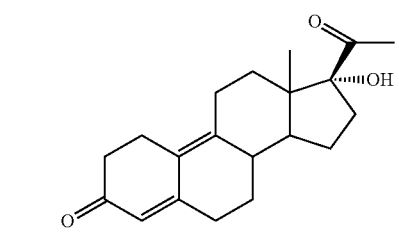 [SMILES: CC(=O)[C@@]1(O)CCC2C3CCC4=CC(=O)CCC4=C3CCC21C]

A preferred embodiment 9, preparing the compound V:

adding the 17α-[(±)1-(1-ethoxyl)ethyl]oxyl-17β-cyano-3,3-ethylendioxyl-5(10),9(11)-dien (10.0 g, 24.2 mmol), anhydrous THF (100 ml) in the reaction bulb and cooling in the icy water, then stirring for 4 h after 1.0M methyl lithium 2-methyl tetrahydrofuran (48.4 ml, 48.4 mmol) is added at 0~10° C., adding 10 ml the 4N HCl and stirring for 30 min, waiting for separating out the organic phase and extracting the aqueous phase by the ethyl acetate, combining the organic phase, drying, concentrating in the vacuo and crystallizing from the ethyl acetate:petroleum ether for obtaining 5.4 g the off-yellow powder, wherein the mp: 185~188° C., the yield is 71%;

wherein utilizing 1.6M methyl lithium ethyl ether for reacting, the similar result can be obtained.

A preferred embodiment 10, preparing the compound V:
utilizing the same method as in the preferred embodiment 9, wherein utilizing anhydrous ethyl ether and the 1.6M methyl lithium ethyl ether for reacting, the similar result can be obtained, the yield is 74%.

A preferred embodiment 11, preparing the compound V:
utilizing the 17α-[(±)1-(1-ethoxyl)ethyl]oxyl-17β-cyano-3,3-ethylendioxyl-5(10),9(11)-dien (4.0 g, 9.68 mmol) as the starting material, stirring for 2 h with the temperature kept after replacing the methyl lithium with a new-prepared methyl Grignard reagent, wherein 2.1 g the off-yellow powder is obtained by the treatments the same as in the preferred embodiment 9, the yield is 68%.

A preferred embodiment 12, preparing the compound V:
utilizing the 17α-[(±)1-(1-n-propyl oxyl)ethyl]oxyl-17β-cyano-3,3-ethylendioxyl-19-norpregna-5(10),9(11)-diene (8.0 g, 18.7 mmol) as the starting material, wherein 4.0 g the off-yellow powder is obtained by the treatments the same as in the preferred embodiment 9, the yield is 70%.

A preferred embodiment 13, preparing the compound V:
utilizing the 117α-[(±)1-(1-isobutyl oxyl)ethyl]oxyl-17β-cyano-3,3-ethylendioxyl-19-norpregna-5(10),9(11)-diene (10.0 g, 22.7 mmol) as the starting material, wherein 4.7 g the off-yellow powder is obtained by the treatments the same as in the preferred embodiment 9, the yield is 67%.

A preferred embodiment 14, preparing the compound V:
utilizing the compound (21.3 g, 50.1 mmol) prepared in the preferred embodiment 7 as the starting material, wherein 11.2 g the off-yellow powder is obtained by the treatments the same as in the preferred embodiment 9, the yield is 72%.

A preferred embodiment 15, preparing the compound V2:
adding the 1.6M methyl lithium ethyl ether (380 ml, 0.61 mol) into the 17α-[(±)1-(1-ethoxyl)ethyl]oxyl-17β-cyano-3,3-ethylendioxyl-5(10),9(11)-dien (50.0 g, 0.121 mmol) and the ethyl ether (500 ml) at 0~10° C., then stirring the reaction mixture for 4 h and pouring into the ice water for separating out the organic phase, extracting the aqueous phase by the ethyl acetate ether until no product is generated, combining the organic phase with the aqueous phase and washing once with water and drying, then concentrating in vacuuming the organic and aqueous phase until a constant weight is about for obtaining 58 g the product, after drying, adding 20-fold acetone, then adding 80 ml the 4N HCl and stirring for 8 h at 25° C., pouring the reaction mixture into they times ice water, extracting the aqueous phase by the dichloromethane, combining the organic phase with the aqueous phase, washing once by saturated sodium bicarbonate and once by the water, drying and concentrating in the vacuo, adding 50 ml the ethyl acetate and cooling, then stirring for 30 min and filtering the precipitated crystalline off for obtaining 27.4 g off-yellow solids, wherein the mp: 195~199° C., the yield is 72%; the solid is displayed as the compound V2 by the TLC, the HPLC is 98%.

A preferred embodiment 16, preparing the compound V:
adding the compound III (1.5 kg, 4.40 mol) in the THF (7.5 L), p-toluenesulfonic acid (5 g) and ethyl vinyl ether (632 ml, 6.6 mol) at the room temperature and cooling in the icy water, stirring the reaction mixture for 3 h at the room temperature, cooling to 0° C. and modifying a PH to neutral with the triethylamine, stirring for 8 h with the temperature kept after 1.6M methyl lithium ethyl ether (8.0 L, 12.8 mol) is added at 0~10° C., adding 300 ml 2N HCl slowly and stirring for 4 h at 25° C., waiting for separating out an organic phase and extracting the aqueous phase by the acetic ether, wherein the aqueous phase is extracted six times, and 600 ml for once, combining, washing and drying the organic phase with the aqueous phase, then decompressing and concentrating in the vacuo the organic and aqueous phase until the constant weight is reached, dissolving by heating and adding the acetic ether, wherein the volume of the acetic ether is five times of the volume of the organic and aqueous phase, cooling and filtering the precipitated crystalline off for obtaining 1036 g the off-yellow powder, wherein the mp: 183~187° C., the yield is 75%, the HPLC shows that about 15% of the product is V1 and about 83% of the product is V2.

A preferred embodiment 17, preparing 3,3,20,20-bis(ethylendioxyl)-17α-hydroxyl-19-norpregna-5(10),9(11)-diene (a compound VI):
adding the compound V (1035 g, 3.30 mol) in the dichloromethane (11 L), ethylene glycol (1000 ml, 17.9 mol), trimethyl orthoformate (1400 ml, 8.4 mol) and p-toluenesulfonic acid (30 g, 0.15 mol) into a reaction kettle, adding the p-toluenesulfonic acid (30 g, 0.15 mol) at 25° C., wherein the starting material disappears after reacting for 5 h at the room temperature, pouring the reaction mixture a reacting liquid into the saturated sodium bicarbonate (5 kg) and stirring for 30 min, wherein the aqueous phase is extracted by 2 L, combining the organic phase and washing with water, then drying the organic phase with the anhydrous magnesium sulfate, concentrating in the vacuo the organic and aqueous phase at 40° C. after adding 10 ml pyridine until the dichloromethane disappears, adding 600 ml the methanol, cooling to 0~10° C. and stirring for 30 min, filtering the precipitated crystalline off and drying for obtaining 1192 g the compound VI, wherein the yield is 90%.

A preferred embodiment 18, preparing 3,3,20,20-bis(ethylene-dioxy)-17α-hydroxy-5α,10α-epoxy-19-norpregna-9 (11)-ene (a compound VII):
cooling the compound VI (1190 g, 2.96 mol) in the dichloromethane (12 L), the pyridine (20 ml) and hexafluoroacetone trihydrate (270 ml, 1.93 mol) to 0~5° C., adding 50% H2O2 hydrogen peroxide (970 ml, 20 mol) slowly, keeping the temperature at −5~5° C., stirring for 3~4 h until the starting material disappears, separating out the organic phase, combining the aqueous phase by extracting twice with the dichloromethane, washing once by the sodium thiosulfate aqueous solution (500 ml) with the concentration of 10%, then washing with the water (500 ml*2), drying the organic phase with the anhydrous magnesium sulfate, then concentrating in the vacuo the organic phase until the constant weight of 1310 g (the constant weight is 1237 g according to a theory) is reached, providing the product, 5α,10α-epoxy: 5β,10β-epoxy=8:2, (the product is detected by the HPLC) in a next step without purification.

A preferred embodiment 19, preparing 3,3,20,20-bis(ethylene-dioxy)-5α-17α-dihydroxy-11β-[4-(N,N-dimethylamino)-phenyl-]-19-norpregna-9 (11)-ene (a compound VIII):
adding Mg (165 g, 6.87 mol,) in the 1,2-dichloromethane (2 ml) and the THF (200 ml), adding 4-bromine-N,N-dimethylaniline (1380 g, 6.9 mol) and the THF (3000 ml) slowly in such a manner to keep the temperature between 40~50° C., then stirring the mixture at and reacting for 3 h at 40~50° C. for 3 h for obtaining the gray Grignard reagent, cooling to 25° C., adding the cuprous chloride (43 g, 0.44 mol), cooling and adding the dichloromethane solution (4 L) of the epoxy (the epoxy comprises about 2.3 g the 5α,10α-epoxy) prepared in a preferred embodiment 20 slowly and keeping the temperature between 10 and 20° C., then stirring for 2 h, pouring the reaction mixture into a 3000 ml icy saturated NH$_4$Cl and stirring for 10 min for separating out the reaction mixture, wherein the aqueous phase is extracted by 2000 ml the dichloromethane*5, combining the organic phase and washing three times with the water, then drying the organic phase with the anhydrous magnesium sulfate, concentrating in the vacuo until the organic phase is in a foam, adding 800 ml the ethyl acetate and heating at 70° C. for 10 mins, then cooling to 10~20° C. and stirring for 30 min, filtering the precipitated crystalline off, washing twice with the ethyl acetate and drying for obtaining 957 g off-white powder, wherein the yield of a two-step reaction is 60%, the mp: 230~234° C., the HPLC>95%.

The preferred embodiment 20, preparing 17α-hydroxy-11β-[4-(N,N-dimethylamino)-phenyl-]-19-norpregna-4,9(10)-diene-3,20-dione (compound IX):

adding the compound VIII (950 g, 1.76 mol) prepared in a preferred embodiment 21 and the 2N HCl (4000 ml) into the reaction kettle, stirring at 25° C. for 2 h until the starting material disappears (detecting by the TLC), extracting the reaction mixture five times with the dichloromethane combining and washing the organic phase once with the saturated sodium bicarbonate and once with the water, then drying with the anhydrous magnesium sulfate, filtering and concentrating to about 3000 ml for a further usage.

The preferred embodiment 21, preparing the Ulipristal acetate (I):

adding a dichloromethane solution of the compound IX prepared in a preferred embodiment 22 and the anhydrous acetic acid (200 ml, 3.50 mol) into the reaction kettle, cooling to −10° C. and adding 70% perchloric acid (237 ml, 3.92 mol), then adding acetic anhydride (1400 ml, 14.9 mol) slowly at 0~10° C. while stirring with the temperature kept for 1~2 h, adding 3 kg icy water for separating out the organic phase, extracting the aqueous phase with 500 ml the dichloromethane*6 the aqueous phase six times and 500 ml for once with the dichloromethane, combining and washing once with 800 ml the saturated sodium bicarbonate and once with 800 ml the water, then drying with the anhydrous magnesium sulfate, filtering, concentrating in the vacuo until the constant weight is reached, adding 800 ml isopropanol and stirring for 30 min, filtering and dry at 60° C. for obtaining 790 g the off-yellow solids, then dissolving by heating with 8000 ml isopropanol:ethanol (95:5), decolourizing and filtering with 1% activated carbon, cooling to 10° C. and stirring for 1 h, filtering and drying at 60° C. for obtaining 586 g the off-yellow solids, wherein the mp: 151~153° C., the Ulipristal acetate is confirmed by a structure, the yield is about 70%, the HPLC>99%.

The preferred embodiment 22, preparing the Ulipristal acetate (I):

adding the 3,20-diketal (100 g, 0.25 mol) compound VI in dichloromethane (1 L), the pyridine (5 ml) and the hexafluoroacetone trihydrate (20 ml, 143 mmol) and cooling to −10~0° C., adding the 50% H2O2 (70 ml, 1.44 mol) slowly, reacting at −5~5° C. for 3~4 h until the starting material disappeared, separating out the organic phase, combining the aqueous phase by extracting twice with the dichloromethane, washing the combined organic phase once by with the 10% sodium thiosulfate (10 ml), washing the organic phase with the water (50 ml for once, then drying with the anhydrous magnesium sulfate, then filtering and concentrating in the vacuo to a volume of 200 ml, wherein the obtained solution is used in the next step;

adding the Mg (9.6 g, 0.4 mol) in the 1,2-dichloromethane (1 ml) and the THF (50 ml) into a three-neck flasks, adding the solution of the 4-bromine-N,N-dimethylaniline (71 g, 0.35 mol) and the THF (200 ml) slowly, stirring and reacting for 3 h at 40~50° C. for obtaining the gray Grignard reagent, cooling to 25° C., stirring at 25° C. for 30 min after adding the cuprous chloride (3 g, 30 mol), cooling and adding the dichloromethane solution of the epoxide at 10~20° C., and stirring for 2 h with the temperature kept, pouring into a 500 ml icy saturated NH$_4$Cl and stirring for 10 min for separating out the organic phase, wherein the aqueous phase is extracted by the dichloromethane 5 times, combining the organic phase and adding 1000 ml saturated NHCl solution, then stirring for 2 h at 25° C. for separating out the organic phase, wherein the aqueous phase is extracted by the dichloromethane 3 times (200 ml*3), combining the organic phase, then washing the organic phase once with the saturated sodium bicarbonate and once with the water, drying the organic phase with the anhydrous magnesium sulfate, decompressing and concentrating the organic phase and pouting into the reaction kettle, adding the anhydrous acetic acid (18 ml, 315 mmol) and 70% the perchloric acid (24 ml, 295 mol) and cooling to −10~0° C., stirring and adding the acetic anhydride (140 ml, 1.49 mol) slowly at −10~0° C., stirring for 30 min with the temperature kept, wherein the aqueous phase is extracted by the dichloromethane 3 times, combining the organic phase, then washing the organic phase once with the saturated sodium bicarbonate and once with the water, then drying the organic phase with the anhydrous magnesium sulfate, decompressing and concentrating the organic phase until the constant weight of 110 g is reached, recrystallization with the 10-fold ethanol:isopropanol (95:5) reagent for obtaining 61.2 g the off-yellow crystal, wherein the mp: 145~148° C.; the yield is 52%, the HPLC>97%; recrystallizing again with the ethanol:isopropanol (95:5) reagent and drying at 60° C. for obtaining 46.0 g the off-yellow crystal, wherein the Ulipristal acetate is confirmed by the structural testing, the yield is 75%, the HPLC>99%.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for preparing Ulipristal acetate, comprising reaction steps of:

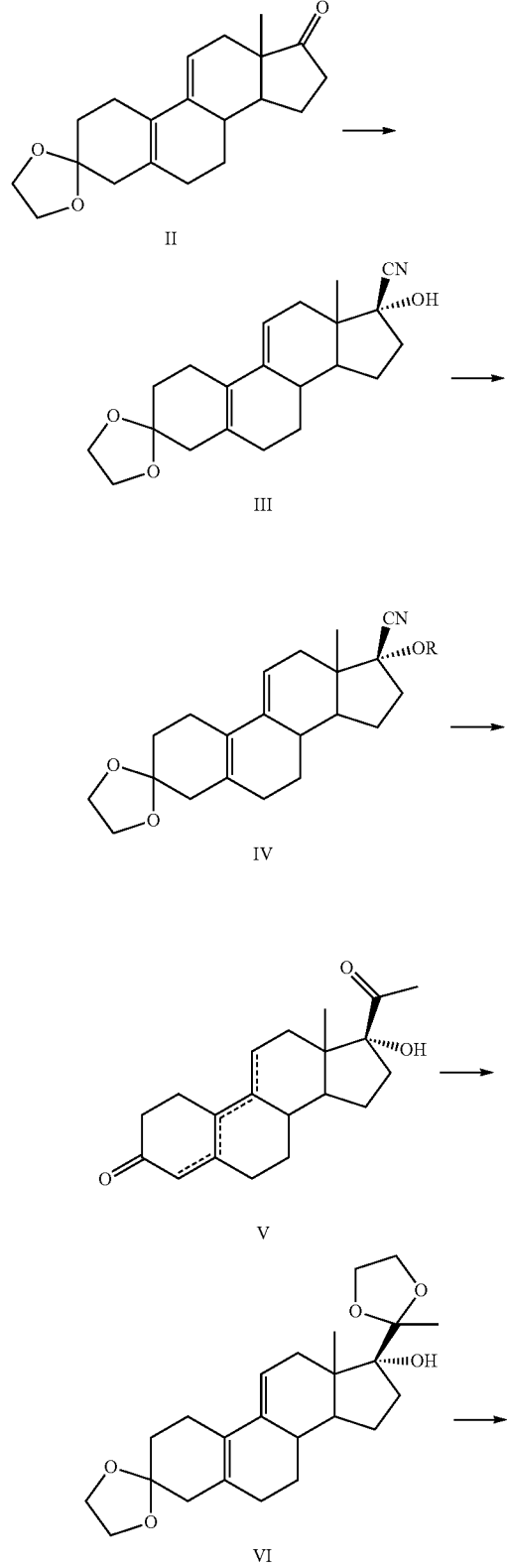

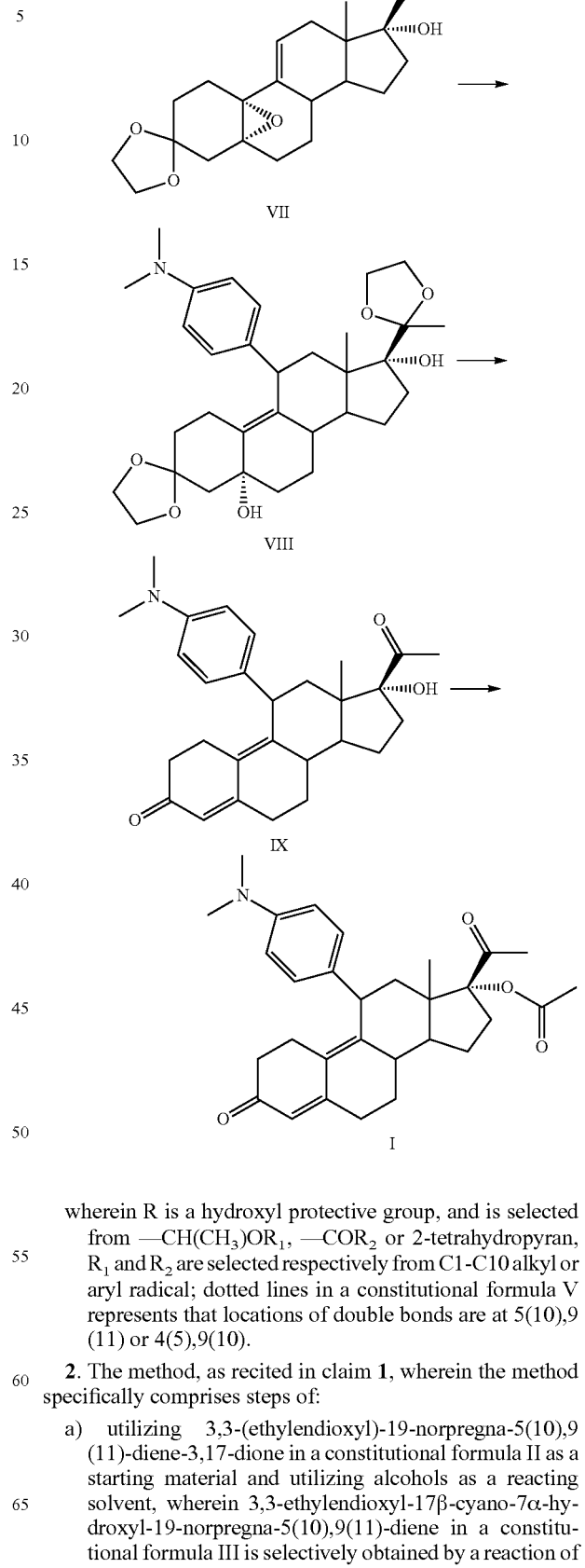

wherein R is a hydroxyl protective group, and is selected from —CH(CH$_3$)OR$_1$, —COR$_2$ or 2-tetrahydropyran, R$_1$ and R$_2$ are selected respectively from C1-C10 alkyl or aryl radical; dotted lines in a constitutional formula V represents that locations of double bonds are at 5(10),9(11) or 4(5),9(10).

2. The method, as recited in claim 1, wherein the method specifically comprises steps of:
a) utilizing 3,3-(ethylendioxyl)-19-norpregna-5(10),9(11)-diene-3,17-dione in a constitutional formula II as a starting material and utilizing alcohols as a reacting solvent, wherein 3,3-ethylendioxyl-17β-cyano-7α-hydroxyl-19-norpregna-5(10),9(11)-diene in a constitutional formula III is selectively obtained by a reaction of the starting material and a cyanation reagent under a weak acidic condition at a temperature between −10° C. to room temperature;

b) obtaining the compound in the constitutional formula IV by the reaction of the compound in the constitutional formula III and a hydroxy protective group reagent under the acid condition in a solvent;

c) hydrolyzing the compound in the constitutional formula IV under the acid condition after the reaction of the compound in the constitutional formula IV with a methylation reagent for obtaining the 5(10),9(11)-diene-3,20-dione in the constitutional formula V or 4(5),9(10)-dienen-3,20-dione or a mixed compound comprising both;

d) catalyzing the reaction of the compound in the constitutional formula V and the ethylene glycol with the p-toluenesulfonic acid and the trimethyl orthoformate or the triethyl orthoformate at the room temperature in dichloromethane for obtaining 3,3-(ethylendioxyl)-17α-hydroxyl-19-norpregna-5(10),9(11)-diene in a constitutional formula VI;

e) epoxidizing the compound in the constitutional formula VI by hydrogen peroxide for obtaining 3,3,20,20-bis(ethylendioxyl)-17α-hydroxyl-5,10-epoxy-19-norpregna-9(11)-ene in a constitutional formula VII;

f) providing the addition reaction of the compound in the constitutional formula VII and a 4-(N,N-dimethyl amidogen) phenylmagnesium bromide Grignard reagent by cuprous chloride for obtaining 3,3,20,20-bis(ethylendioxyl)-5α-17α-dyhydroxyl-11β-[4-(N,N-dimethylamino)-phenyl-]-19-norpregna-9 (11)-ene in a constitutional formula VIII;

g) hydrolyzing the compound in the constitutional formula VIII under an acidic condition for obtaining 17α-hydroxyl-11β-[4-(N,N-dimethylamino)-phenyl-]-19-norpregna-9(11)-diene-3,20-dione in a constitutional formula IX; and h) acetylating the compound in the constitutional formula IX with the acetic acid, perchloric acid and acetic anhydride at 0~10° C. in the dichloromethane for obtaining the Ulipristal acetate in a constitutional formula I.

3. The method, as recited in claim 1, wherein the compound in the constitutional formula III reacts with the hydroxyl protective group reagent for obtaining the compound in the constitutional formula IV, the alkali is directly added for modifying a pH value to neutral or alkaline without separation, then the compound in the constitutional formula IV reacts with the methyl lithium or the methyl Grignard reagent, the product is hydrolyzed in the solvent under the acid condition right after the reaction or after being processed for obtaining the compound V.

4. The method, as recited in claim 2, wherein the compound in the constitutional formula III reacts with the hydroxyl protective group reagent for obtaining the compound in the constitutional formula IV, the alkali is directly added for modifying a pH value to 7~8 without separation, then the compound in the constitutional formula IV reacts with the methyl lithium or the methyl Grignard reagent, the product is hydrolyzed in the solvent under the acid condition right after the reaction or after being processed for obtaining the compound V.

5. The method, as recited in claim 2, wherein the methylation reagent is methyl lithium or methyl Grignard reagent.

6. A compound in the constitutional formula IV, comprising:

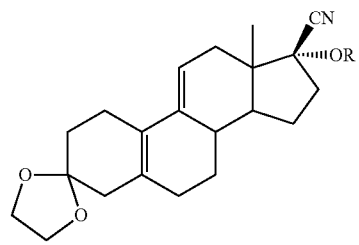

and an isomer or a racemic modifications thereof, wherein R is defined in claim 1.

7. The compound, as recited in claim 6, wherein said compound is selected from:

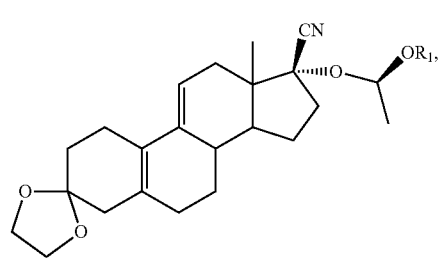

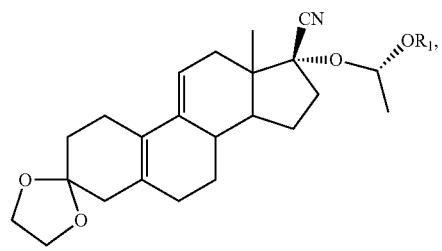

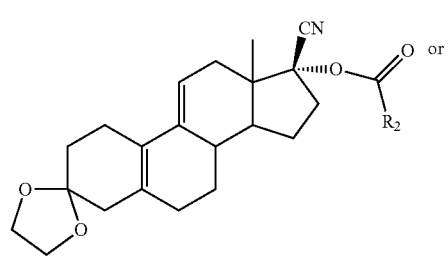

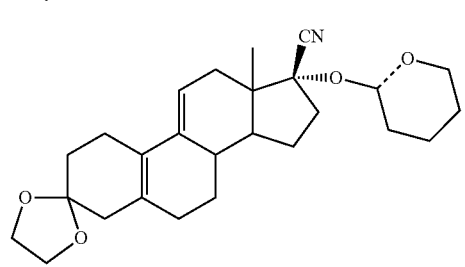

and said isomer or said racemic modifications thereof; wherein dot and line keys are respectively a R or S configuration or said racemic modifications; $R_1$ and $R_2$ are selected respectively from C1-C10 alkyl or aryl radical.

8. The compound, as recited in claim 6, wherein said compound is selected from:

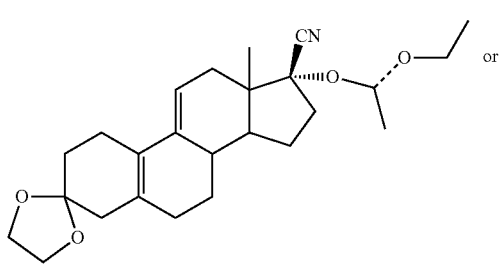

or

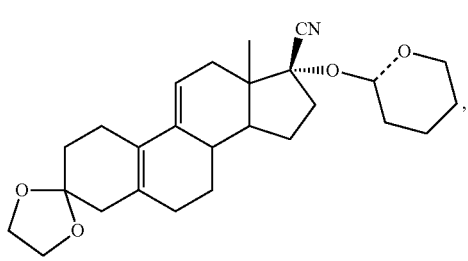

IV4

, wherein said dot and line keys are respectively said R or S configuration or said racemic modifications.

9. The compound, as recited in claim 7, wherein said compound is selected from:

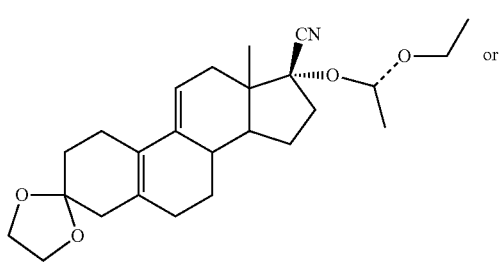

or

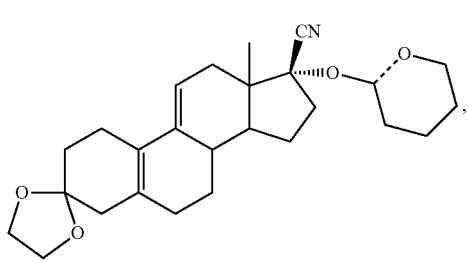

IV4

, wherein said dot and line keys are respectively said R or S configuration or said racemic modifications.

10. A method for preparing said compound in the constitutional formula IV recited in claim 6, comprising a step of: providing a reaction of said compound in the constitutional formula III and said hydroxyl protective group for obtaining said compound in the constitutional formula IV:

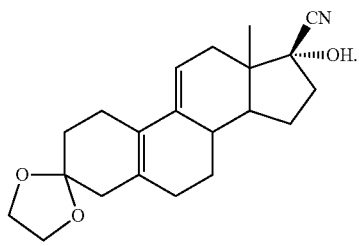

III

11. The method, as recited in claim 10, wherein the hydroxyl protective group reagent is selected from the acid anhydride, the acid, the acyl chloride, vinyl ether or 2,3-dihydropyran, preferably, the vinyl ether is selected form ethyl vinyl ether, n-propyl vinyl ether, n-butyl vinyl ether, isobutyl vinyl ether and methyl vinyl ether.

12. A method for preparing said compound in the constitutional formula V, comprising:

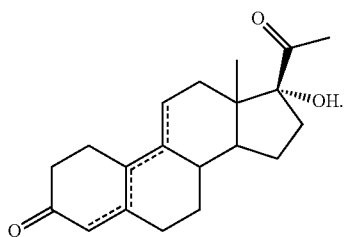

V wherein dotted lines represents that locations of double bonds are at 5(10),9(11) or 4(5),9(10);

wherein the method comprises a step of: hydrolyzing the compound in the constitutional formula IV under the acidic condition after the compound in the constitutional formula IV reacts with a methylation reagent for obtaining the compound in the constitutional formula V:

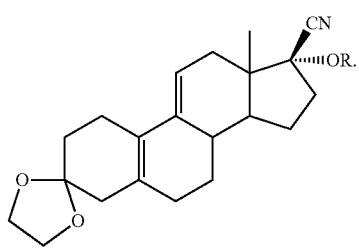

IV

13. The method, as recited in claim 12, wherein the methylation reagent is methyl lithium or methyl Grignard reagent.

* * * * *